United States Patent [19]
Hasegawa et al.

[11] Patent Number: 5,766,572
[45] Date of Patent: Jun. 16, 1998

[54] WATER-SOLUBLE CARBOXYPOLYSACCHARIDE-MAGNETIC IRON OXIDE COMPLEX HAVING A SMALL PARTICLE DIAMETER

[75] Inventors: Masakatsu Hasegawa; Yoshio Ito, both of Nagoya; Hisato Yamada, Toyota; Hideo Nagae, Kasugai; Nahoko Tozawa, Seto; Yukari Hino; Kyoji Kito, both of Nagoya; Shusaburo Hokukoku, Kani, all of Japan; Rudiger Lawaczeck, Berlin, Germany; Wolfgang Ebert, Berlin, Germany; Detlef Pfefferer, Berlin, Germany; Susanne Wagner, Berlin, Germany; Mayk Kresse, Berlin, Germany

[73] Assignee: Meito Sangyo Kabushiki Kaisha, Japan

[21] Appl. No.: 379,586

[22] PCT Filed: Aug. 4, 1993

[86] PCT No.: PCT/JP93/01092
§ 371 Date: Feb. 6, 1995
§ 102(e) Date: Feb. 6, 1995

[87] PCT Pub. No.: WO94/03501
PCT Pub. Date: Feb. 17, 1994

[30] Foreign Application Priority Data

Aug. 5, 1992 [JP] Japan ................... 4-227792

[51] Int. Cl.⁶ ................................................. A61B 5/055
[52] U.S. Cl. ............... 424/9.322; 424/493; 436/173
[58] Field of Search .................. 424/9.322, 646, 424/648, 493; 436/173; 128/653.4, 654

[56] References Cited

U.S. PATENT DOCUMENTS

| | | | |
|---|---|---|---|
| 4,101,435 | 7/1978 | Hasegawa et al. | 252/62.53 |
| 4,335,094 | 6/1982 | Mosbach | 424/1 |
| 4,452,773 | 6/1984 | Molday | 424/1.1 |
| 4,675,173 | 6/1987 | Widder | 424/9.322 |
| 4,827,945 | 5/1989 | Groman et al. | 424/9.32 |
| 4,849,210 | 7/1989 | Widder | 424/9.322 |
| 4,863,715 | 9/1989 | Jacobsen et al. | 424/9.322 |
| 4,925,678 | 5/1990 | Ranney | 424/493 |
| 4,951,675 | 8/1990 | Groman et al. | 424/9.32 |

FOREIGN PATENT DOCUMENTS

| | | |
|---|---|---|
| 0 543 020 | 5/1993 | European Pat. Off. |
| 3-141119 | 6/1991 | Japan |
| 3-242327 | 10/1991 | Japan |
| 85/02772 | 7/1985 | WIPO |
| 87/02893 | 5/1987 | WIPO |
| 88/00060 | 1/1988 | WIPO |
| 91/05546 | 5/1991 | WIPO |

OTHER PUBLICATIONS

Cox, JS et al., J. Pharm. Pharmacol. 24:513–517 (1972).
Gries et al., Chem. Abs. 105:120790, (1986).
Kronick et al., Journal of Biochemical and Biophysical Methods, "Use of a superparamagnetic particles for isolation of cells" vol. 12, 1986, pp. 73–80.
Weissleder et al., Radiology, "Ultrasmall Superparamagnetic Iron Oxide: Characterization of a New Class of Contrast Agents for MR Imaging", vol. 175, 1990, pp. 489–493.
Weissleder et al., Radiology "Polyclonal Human Immunoglobulin G Labeled with Polymeric Iron Oxide: Antibody MR Imaging", vol. 181, pp. 245–249.

*Primary Examiner*—Gary E. Hollinden
*Attorney, Agent, or Firm*—Wenderoth, Lind & Ponack

[57] ABSTRACT

A water-soluble carboxypolysaccharide-magnetic iron oxide complex of small particle diameter composed of a water-soluble carboxypolysaccharide and a magnetic iron oxide having a core diameter ranging from about 2 to about 7 nm, wherein the total diameter ranges from about 10 to about 50 nm, the ratio of the total diameter to the core diameter is about 15 or less, and the $T_2$-relaxivity ranges from about 10 to about 150 $(mM.sec)^{-1}$. Said complex has low toxicity and small side effects and is useful in the fields of medical treatment, biology and engineering as an iron-supplementing agent, an X-ray contrast medium, an MRI contrast medium, a reagent for blood flow rate measurement, a carrier for drug administration, etc.

9 Claims, 4 Drawing Sheets

FIG. 4B

WATER-SOLUBLE CARBOXYPOLYSACCHARIDE-MAGNETIC IRON OXIDE COMPLEX HAVING A SMALL PARTICLE DIAMETER

This Application is a 371 of PCT/JP93/01092 filed Aug. 4, 1993.

TECHNICAL FIELD

The present invention relates to a water-soluble carboxypolysaccharide-magnetic iron oxide complex having a small particle diameter, which is useful in the fields of biology, medical treatment, etc. as a contrast medium for nuclear magnetic resonance imaging (hereinafter abbreviated to MRI), an X-ray contrast medium, etc.

PRIOR ART

A complex of a magnetic iron oxide having a colloid size has superparamagnetism, and an aqueous sol thereof (i.e. a magnetic fluid) has drawn attention in recent years in the fields of medical treatment, biology and engineering as an MRI contrast medium, in particular. When a magnetic iron oxide complex is used as an MRI contrast medium, for example, when the complex is administered intravascularly to allow liver Kupffer's cells to capture it, the complex may have a relatively large particle diameter; in that case, a large particle diameter is rather advantageous because there can be obtained a large $T_2$-relaxivity (the $T_2$-relaxivity is a yardstick for contrast ability). However, when the complex is used as an MRI contrast medium moving between cells and/or tissues, it is desired that the particle diameter of the magnetic iron oxide core and/or the total particle diameter of the complex is small and that the $T_2$-relaxivity is as large as possible.

There have hitherto been made various disclosures with respect to compounds between magnetic iron oxide ultrafine particles and polysaccharide. For example, Japanese Patent Publication No. 13521/1984 (U.S. Pat. No. 4,101,435) discloses a complex between agnetic iron oxide prepared beforehand and dextran or alkali-treated dextran. No specific particle diameter is mentioned in the literature, but the complex obtained by the method described in the Examples of said literature has a core (magnetic iron oxide) diameter of about 7 to about 12 nm and a total diameter of about 80 to about 200 nm when measured by methods described later.

U.S. Pat. No. 4,452,773 discloses microspherical magnetic iron oxide coated with dextran. According to this literature, the core diameter is about 10 to about 20 nm and the total diameter by SEM is about 30 to about 40 nm. P. Kronick and R. W. Gilpin, Journal of Biochemical and Biophysical Methods, 12, 73–80 (1986) reports a dextran-magnetite complex used for cell-separation, particularly antibody-bonding. The core diameter is 3 nm according to the literature, but it is feared that the total diameter is large because of dextran use and that the complex is high in acute toxicity (which is an important property of drug).

Japanese Patent Application Kokai (Laid-Open) No. 141119/1991 discloses a process for producing magnetite ultrafine particles having an average particle diameter of 10 nm or more by controlling the ratio of iron ion during reaction and the reaction temperature. Japanese Patent Application Kokai (Laid-Open) No. 242327/1991 discloses a process for producing magnetic ultrafine particles having a particle diameter of 10–15 nm by controlling the iron ion concentration and dextran concentration during reaction.

Further, R. Weissleder et al., Radiology, 175, 489493 (1990) and R. Weissleder et al., Radiology, 181, 245249 (1991) each disclose an approach to produce a complex of small particle diameter by subjecting a dextran-magnetic iron oxide complex to gel filtration fractionation. However, the obtained complex certainly has a small core diameter, but it is feared that the complex has a large total diameter because of dextran use and the employment of gel filtration fractionation and has strong acute toxicity and low stability. Further problems remain in procedure and yield.

Hence, the present inventors made an extensive study in order to develop a water-soluble carboxypolysaccharide-magnetic iron oxide complex having a small particle diameter (hereinafter abbreviated to "magnetic complex" or simply to "complex" in some cases) which can have wider applications to living bodies, and a process for efficient production of said complex. As a result, the present inventors have newly found out that a magnetic complex having a small core diameter and a small total diameter and further having a relatively large $T_2$-relaxivity can be obtained efficiently. The finding has led to the completion of the present invention.

DISCLOSURE OF THE INVENTION

According to the present invention, there is provided a water-soluble carboxypolysaccharide-magnetic iron oxide complex composed of a water-soluble polysaccharide and ultrafine particles of magnetic iron oxide and having a small particle diameter and a relatively large $T_2$-relaxivity. Herein, the particle diameter refers to both the particle diameter of magnetic iron oxide core and the total diameter of the complex.

According to the present invention, there is specifically provided a water-soluble carboxypolysaccharide-magnetic iron oxide complex of small particle diameter composed of a water-soluble carboxypolysaccharide and a magnetic iron oxide having a core diameter ranging from about 2 to about 7 nm, wherein the total diameter ranges from about 10 to about 50 nm, the ratio of the total diameter to the core diameter is about 15 or less, and the $T_2$-relaxivity ranges from about 10 to about 150 $(mM.sec)^{-1}$.

DETAILED DESCRIPTION OF THE DRAWINGS

FIG. 4 is photographs of in vivo MR images of pelvic wall of hare rabbit, taken (A) before the complex obtained in Example 1 was injected into a rabbit intravenously in an amount of 200μmol (as Fe) per kg of body weight and (B) 24 hours after the intravenous injection.

DETAILED DESCRIPTION OF THE INVENTION

In the present invention, the polysaccharide, which is one component constituting the magnetic complex, is preferably a carboxypolysacchatride in view of the particle diameter, toxicity, safety, yield, etc of the complex. As the material polysaccharide for the carboxypolysaccharide, there can be mentioned, for example, glucose polymers such as dextran, starch, glycogen, pullulan, schizophyllan, lentinan, pestalotian and the like; mannose polymers such as mannan and the like; galactose polymers such as agarose, galactan and the like; xylose polymers such as xylan and the like; and L-arabinose polymers such as arabinan and the like. Of these, dextran, starch and pullulan are preferred with dextran being preferred particularly.

The carboxypolysaccharide includes polysaccharides obtained by converting the reducing end group of a water-soluble polysaccharide into a carboxyl group, and can be produced, for example, by a method of heat-treating a water-soluble polysaccharide with an alkali, particularly sodium hydroxide, or a method of preferentially oxidizing only the reducing end group of a water-soluble polysaccharide by the use of an oxidizing agent such as indolin-sodium hydroxide, sodium hypochlorite or the like. Of these carboxypolysaccharides, a water-soluble polysaccharide obtained by alkali treatment is preferred. In the present invention, therefore, a carboxydextran obtained by subjecting dextran to an alkali treatment is most preferred.

When the water-soluble carboxypolysaccharide used in the present invention has too small a molecular weight, the resulting magnetic complex has high toxicity, low stability and a large total diameter. Also when the water-soluble carboxypolysaccharide has too large a molecular weight, the magnetic complex has similar properties. Therefore, it is appropriate that the water-soluble carboxypolysaccharide has an intrinsic viscosity of generally about 0.03-about 0.2 dl/g, preferably about 0.04 to about 0.15 dl/g, more preferably about 0.05 to about 0.1 dl/g. In the present specification, the intrinsic viscosity [η] of water-soluble carboxypolysaccharide is a value obtained when measured at 25° C. according to the method disclosed in Viscosity Measurement Method, Item 35, General Tests, The Pharmacopeia of Japan (Twelveth Edition, 1991).

The magnetic iron oxide, which is the other component constituting the magnetic complex of the present invention, is prepared preferably by treating an aqueous solution of two or more iron salts with an alkali. With respect to the combination of iron salts used for formation of the magnetic iron oxide, there can be cited, for example, an aqueous mixed iron salt solution containing a ferrous salt and a ferric salt. In this case, the molar ratio of the ferrous salt and the ferric salt is generally about 1:19 to about 1:1.5, preferably about 1:9 to about 1:2. As the molar ratio of the ferrous salt and the ferric salt is smaller, the total diameter, core (magnetic iron oxide particles) diameter and $T_2$-relaxivity of the resulting complex are smaller generally; in the present invention, therefore, the molar ratio can be determined experimentally depending upon the purpose, application, etc. of the complex. Incidentally, part, for example, about half or less of the ferrous salt can be replaced by salt(s) of other bivalant metal(s), for example, a salt of at least one metal selected from magnesium, zinc, cobalt, manganese, nickel, copper, barium, strontium, etc. The thus obtained magnetic complex also is included in the present invention. As the kinds of salts, there can be mentioned, for example, salts with mineral acids such as hydrochloric acid, sulfuric acid, nitric acid and the like.

The complex of the present invention can advantageously be obtained in one step by mixing, with stirring, an aqueous mixed iron salt solution containing a ferrous salt and a ferric salt, with an aqueous alkali solution in the presence of a water-soluble carboxypolysaccharide generally for about 30 minutes or less, preferably for about 5 minutes or less, more preferably about 1 minute or less to give rise to a reaction. In this case, the time period refers to a time from the start of addition or mixing of the aqueous mixed iron salt solution and the aqueous alkali solution, to the completion of the addition or mixing. As the addition or mixing time is shorter, the resulting complex has a smaller core diameter and a smaller total diameter, and its $T_2$-relaxivity is not so small as compared with the smallnesses of said diameters. The stirring conducted during the reaction is preferably made at such a rate that each solution added for the reaction is dispersed in the reaction system substantially simultaneously with the dropping of each solution into the system, because individual components are desired to become quickly uniform in the reaction system. Continued stirring is preferred during the reaction. Desirably, the mixed iron salt contains a ferrous iron salt and a ferric iron salt at a given ratio during the reaction with an alkali.

The above process for obtaining the present complex can be classified, depending upon the addition order of solutions, into (A) a process which comprises adding an aqueous mixed iron salt solution to an aqueous solution of a water-soluble carboxypolysaccharide and then adding an aqueous alkali solution to give rise to a reaction; (B) a process which comprises adding an aqueous alkali solution to an aqueous solution of a water-soluble carboxypolysaccharide and then adding an aqueous mixed iron salt solution to give rise lo a reaction; (C) a process which comprises adding to an aqueous alkali solution a mixture of an aqueous mixed iron salt solution and an aqueous solution of a water-soluble carboxypolysaccharide; (D) a process which comprises adding to an aqueous mixed iron salt solution a mixture of an aqueous alkali solution and an aqueous solution of a water-soluble carboxypolysaccharide; and so forth. These processes (A), (B), (C) and (D) differ only in the addition orders and do not differ substantially in other reaction conditions.

The amount of the water-soluble carboxypolysaccharide used in the present complex can be generally about 1 to about 15 times, preferably about 3 to about 12 times, more preferably about 7 to about 10 times the weight of the iron in the iron salt used. The concentration of the polysaccharide is not strictly restricted, but is appropriately in the range of generally about 1 to about 40 w/v %, preferably about 5 to about 30 w/v %. The concentration of the aqueous mixed iron salt solution can be varied in a wide range but is appropriately in the range of generally about 0.1 to about 3M, preferably about 0.5 to about 2M.

As the aqueous alkali solution, there can be used, for example, at least one alkali selected from alkali metal hydroxides such as NaOH, KOH and the like; amines such as ammonia, triethylamine and the like; and so forth. Of these, an aqueous NaOH or ammonia solution is preferred. The concentration of the aqueous alkali solution also can be varied in a wide range but is appropriately in the range of about 0.1 to about 10N, preferably about 1 to about 5N. The amount of the alkali used is such an amount that the pH of the reaction system after the addition of all solutions becomes roughly neutral to about 12, or the ratio of the iron salt and the alkali becomes about 1:1 to about 1:1.5 in terms of normality ratio.

The addition of the individual aqueous solutions and mixing thereof can be conducted with stirring, generally at room temperature to about 100°C., preferably at about 40° to about 95° C. As necessary, an alkali or an acid (e.g. a mineral acid) is added for pH adjustment; then, heating and refluxing is conducted at about 30 to about 120° C. for about 10 minutes to abut 5 hours, generally for about 1 hour. Thereby, the reaction for formation of a water-soluble carboxypolysaccharide-magnetic iron oxide complex can be completed.

Of the above processes (A), (B), (C) and (D) different in addition orders, the processes (A) and (D) are preferred to the processes (B) and (C) for the reasons of the high yield of complex and the high level of $T_2$-relaxivity as compared with the level of total diameter. The process (A) is particularly preferred.

One of the advantages of the above production processes of the present invention is that the physical properties of the magnetic complex obtained are determined substantially by the synthesis conditions and that a complex small in core diameter and total diameter and relatively large in $T_2$-relaxivity can be obtained at a high yield, for example, by using no gel filtration fractionation.

The process of adding and mixing two solutions, i.e. an aqueous solution of a water-soluble carboxypolysaccharide and a mixed iron salt and an aqueous alkali solution, or three solutions, i.e. an aqueous water-soluble carboxypolysaccharide solution, an aqueous mixed iron salt solution and an aqueous alkali solution, at given rates can be said to be a particularly preferable process of the present invention because the addition time is substantially zero minute.

Then, the purification and adjustment of the complex formed is conducted. It can be conducted by using one or a combination of two or more of various methods each known per se. For example, the reaction mixture containing a complex is mixed with an organic solvent miscible with water, for example, a poor solvent to the complex, such as methanol, ethanol, acetone or the like to preferentially precipitate the complex; and the precipitate is separated. This precipitate is dissolved in water, subjected to dialysis against running water or the like, and concentrated as necessary by an ordinary method, whereby a complex aqueous sol having a desired purity and concentration can be obtained. The complex aqueous sol can be subjected to a heat treatment as necessary. The heat treatment can appropriately be conducted generally at about 60° to about 140° C. for about 5 minutes to about 5 hours and, when sterilization is required, at 121° C. for about 20 to about 30 minutes. Further, as necessary, before or after the heat treatment, it is possible to add various auxiliary agents which are physiologically acceptable, for example, an isotonic agent such as inorganic salt (e.g. sodium chloride), monosaccharide (e.g. glucose) or sugaralcohol (e.g. mannitol or sorbitol) and a pH-keeping agent such as phosphate buffer solution or tris buffer solution.

In other purification method, the reaction mixture is subjected to ultrafiltration to separate and remove unreacted water-soluble carboxypolysaccharide and low-molecular compounds; a given amount of a water-soluble carboxypolysaccharide is added as necessary; thereby, a complex aqueous sol having a desired purity and concentration can be obtained. In any purification methods, pH adjustment, centrifugation and/or filtration step can be added as necessary in the course of or after the above procedure. The purified complex aqueous sol can be made into a complex powder, for example, by spray-drying or freeze-drying, or by adding thereto an organic solvent miscible with water, such as methanol, ethanol, acetone or the like and drying the resulting precipitate under reduced pressure. The thus-obtained powder can easily be returned to an aqueous sol by the addition of water.

The ratio of water-soluble carboxypolysaccharide and magnetic iron oxide in the above-obtained complex depends upon the diameter of magnetic iron oxide particles, the molecular weight of water-soluble carboxypolysaccharide, etc. and can be varied in a wide range. When the ratio is large, the resulting aqueous sol has a high absolute viscosity; when the ratio is small, the total diameter of complex is large owing to the agglomeration of complex particles and the stability of complex is inferior. Hence, in general, the complex can contain the water-soluble carboxypolysaccharide in an amount of about 0.2 to about 5 parts by weight, preferably about 0.5 to about 3 parts by weight, more preferably about 1 to about 2 parts by weight per 1 part by weight of the iron present in the magnetic iron oxide.

The metal amount in the complex of the present invention [which refers to the total amount of the iron and other metal(s) (if present) contained in the magnetic iron oxide] is a value obtained when measured by the method described in Atomic Absorption Spectroscopy, Item 20, General Tests, The Pharmacopeia of Japan (The 12th Revision, 1991). That is, concentrated hydrochloric acid is added to a complex aqueous sol or a complex powder; the metal(s) contained in the complex is (are) decomposed until said metal(s) becomes (become) a chloride (chlorides) completely; the reaction mixture is diluted appropriately; the resulting solution is subjected to atomic absorption spectroscopy using standard solution(s) containing the same metal(s) to determine the total amount of the metal(s) contained in the complex.

The amount of the water-soluble carboxypolysaccharide in the complex is a value obtained when measured by the sulfuric acid-anthrone method according to the method described in Analytical Chem., 25, 1656 (1953). That is, the decomposed solution with hydrochloric acid, obtained in the above measurement of the amount of iron and other metal(s) is diluted appropriately; to the resulting solution is added a sulfuric acid-anthrone reagent to develop a color; and the absorbance is measured. Simultaneously, a color is developed in the same manner using the water-soluble carboxypolysaccharide used in the production of the complex, as a standard substance; and the absorbance is measured. A ratio of these two absorbances is calculated to determine the amount of the water-soluble carboxypolysaccharide.

The particle diameter of the magnetic iron oxide which is the core of the complex, is determined using an X-ray diffractometer (target: Co, wavelength: 1.790 Å). Since when the complex powder of the present invention obtained by freeze-drying is subjected to X-ray diffraction, several diffraction peaks corresponding to a specific compound can be observed, it is learned that the magnetic iron oxide contained in the complex exists in a crystalline form. The above diffraction peak is broader, namely, smaller as the diameter of the magnetic iron oxide contained in the complex is smaller. Thus, in the case where the particle diameter of the magnetic iron oxide contained in the complex is 0.1 µm or less, the particle diameter can be measured by X-ray diffraction. That is, the particle diameter (i.e. core diameter) can be obtained by the following Scherrer formula for the strongest peak in X-ray diffraction.

$$D = k\lambda/\beta \cdot \cos\theta,$$

$$\beta = (B^2 - b^2)^{1/2}$$

wherein

D: particle diameter (Å)

k: constant, 0.9

λ: X-ray wavelength (1.790 Å)

θ: Bragg angle (degree)

B: half-width of sample (radian)
b: half-width of standard sample (radian)
In the above, the standard sample to be used is a magnetite having a particle diameter of 1 μm or more.

The total diameter of the magnetic complex of the present invention is a value obtained when measured by the use of a dynamic light-scattering photometer, DLS-700 manufactured by Ohtsuka Electronic Co. according to a dynamic light-scattering method [refer to, for example. Polymer J., 13, 1037–1043 (1981)].

The complex of the present invention is not a mere mixture but a compound of magnetic iron oxide and a water-soluble carboxypolysaccharide. This can be understood, for example, from the facts that when an aqueous sol of the magnetic iron oxide complex of the present invention is fractionated using a gel filtration column, an elution peak is observed at an elution point of higher molecular weight than the molecular weight of the water-soluble carboxypolysaccharide and, when the peak is analyzed, both a saccharide and iron are detected in the peak, and that when in the preparation step for the magnetic complex, purification is carried out using an ultrafiltration membrane having a pore diameter capable of passing particles smaller than the complex particles, the ratio of saccharide to iron in the remaining aqueous sol gradually converges to a certain value. Incidentally, in the gel filtration pattern of the complex of the present invention, a peak of a carboxypolysaccharide is generally seen in addition to the peak in which both a saccharide and iron are present.

The magnetism (for example, magnetization and coercive force) of the magnetic complex of the present invention can be determined from a magn.etization-magnetic field curve (so-called M-H curve) depicted using a vibrating sample magnet meter at room temperature. Further, the coercive force of the complex of the present invention is about 5 oersteds or less and the complex is substantially superparamagnetic.

The $T_2$-relaxivity of the magnetic complex of the present invention can be determined by depicting the resonance curves of the proton of water on aqueous sols obtained by diluting the complex of the present invention with water so as to give various concentrations and on the water used for the dilution, by the use of CW-NMR of 60 MHz (the magnetic field being about 1.4 teslas); determining the half-width $\Delta v^{1/2}$ (unit: Hz) of the obtained peak; calculating $1/T_2$ (unit: sec$^{-1}$)=$\pi \cdot \Delta v^{1/2}$, plotting the relation of $1/T_2$ to the iron concentration (unit: mM) in the aqueous sol of the test sample, and determining the $T_2$-relaxivity [unit: (mM.sec)$^{-1}$] from the inclination of the straight line determined by least square method.

In the water-soluble carboxypolysaccharide-magnetic iron oxide complex of the present invention, the core diameter, the total diameter, the ratio of total diameter/core diameter and the $T_2$-relaxivity can be respectively, in the ranges of generally about 2 to about 7 nm, about 10 to about 50 nm, about 15 or less, and about 10 to about 150 (mM.sec)$^{-1}$; preferably about 3 to about 6 nm, about 15 to about 40 nm, about 10 or less, and about 15 to about 120 (mM.sec)$^{-1}$; more preferably about 3 to about 5 nm, about 15 to about 30 nm, about 7 or less, and about 15 to about 100 (mM.sec)$^{-1}$. Also in the present complex, the magnetization at 1 tesla can be in the range of generally about 10 to about 100 emu, preferably about 20 to about 90 emu per g of the iron contained in the complex.

The complex of the present invention, when obtained by making small the molar ratio of ferrous iron to ferric iron and further making short the addition or mixing time, as compared with when obtained by only making small said molar ratio, has an advantage that the degree of reduction in $T_2$-relaxivity is small as compared with the decreases in the diameter of magnetic iron oxide core particles and the total diameter of complex. For example, when the complex of Example 8 (described later) obtained by using a ferrous iron/ferric iron molar ratio of 1:4 and a reaction time of 15 minutes is compared with the complex of Example 9 (described later) obtained by using the same molar ratio and a reaction time of 40 seconds, the diameter of the magnetic iron oxide particles is 6.7 nm and 5.3 nm, respectively; the total diameter is 27 nm and 23 nm, respectively; and the $T_2$-relaxivity is 52 (mM.sec)$^{-1}$ and 64 (mM.sec)$^{-1}$, respectively.

When various conventional magnetic complexes each having a large particle diameter are administered to, for example, rabbits intravenously in the form of an aqueous sol, the rabbits cause significant blood pressure reduction in several minutes and die in some cases. In contrast, with the complex of the present invention, no such blood pressure reduction takes place or blood pressure reduction is very small, and a significant improvement is seen.

It was also found that the complex of the present invention is very low in platelets-agglutinating activity. That is, when various complexes are administered to, for example, rabbits intravenously in the form of an aqueous sol and the ratio of the platelets number in peripheral blood of 5 minutes after administration to the platelets number right before administration, i.e. the retention (%) of platelets is measured, the platelets retention is about 1 to about 10% in the case of complexes of large particle diameter while it is 10% or more in the case of the present complex. For example, the complex of Comparative Example 1 (described later) gives a platelets retention of 3% while the complex of Example 11 (described later) gives a platelets retention of 36%.

When the water-soluble carboxypolysaccharide-magnetic iron oxide complex of the present invention in the form of an aqueous sol is administered to mice intravenously, the acute toxicity $LD_{50}$ of the complex is about 30 to about 80 mmol/kg in terms of the metal. In contrast, the acute toxicities $LD_{50}$ of the magnetic complexes obtained in Comparative Examples are about 5 to about 80 mmol/kg. Thus, it can be seen that the toxicity of the present complex, as compared with those of the complexes of Comparative Examples, is equivalent or very low.

It was found that at least part of the water-soluble carboxypolysaccharide-magnetic iron oxide complex of the present invention administered intravenously accumulates in organs having a well-developed reticuloendothelial system, such as liver. Based on this fact, the metabolism of the present complex was evaluated by measuring the degree of magnetization of liver using CW-NMR. That is, a complex aqueous sol is intravenously administered to rats in an amount of 0.1 mmol/kg as the metal; $1/T_2$ is determined on the rat liver in the same manner as in the measurement of $T_2$-relaxivity at the points of time when, for example, 1 hour, 2 hours, 4 hours, 1 day, 3 days, 7 days and 14 days have elapsed after the administration; correction is made using the $1/T_2$ value of the livers of the non-administered rats group; and then the metabolism of each complex is calculated as half-life from the relation between $1/T_2$ and time after the administration. The half-life of the complex of the present invention is about 2 to about 3 days while those of the complexes obtained in Comparative Examples are about 3 to about 7 days. Thus, these results indicate that the complex of the present invention is metabolized more easily.

As mentioned previously, the complex of the present invention is taken into organs each having a reticuloendothelial system, such as liver, spleen, lymph nodes and bone marrow. The amount of the complex taken into or accumulated in these organs are influenced by the particle diameter of the complex. For example, when the particle diameter is made small, the amount of the complex taken into lymph nodes increases and the inblood half-life of the administered complex is prolonged. In the present invention, the particle diameter of the complex can be varied by appropriately selecting the reaction conditions for production of the complex, there can be prepared a complex having a desired particle diameter and accumulation property.

The complex of the present invention has various excellent properties as mentioned above and can be used in the fields of medical treatment, biology and engineering, for example, as an iron-supplementing agent, an X-ray contrast medium, an MRI contrast medium, a reagent for blood stream measurement and a carrier for drug when the drug is administered to a topical part by the utilization of a magnetic field. The complex of the present invention can be used particularly preferably as an MRI contrast medium for lymph nodes, bone marrow and blood vessel, or as a reagent for measurement of intravascular flow amount in blood vessel, lymph or the like.

When the complex of the present invention is used as an MRI contrast medium, it is desirable to use the complex in the form of an aqueous sol. Although the concentration of the complex can be varied over a wide range, the concentration can be in the range of, for example, generally about 1 mmol/l to about 4 mol/l, preferably about 0.01 to about 2 mol/l in terms of the metal. In the preparation of the aqueous sol, it is possible to add various physiologically acceptable auxiliaries, for example, an inorganic salt (e.g. sodium chloride), a monosaccharide (e.g. glucose), a sugaralcohol (e.g. mannitol or sorbitol), a phosphate buffer agent and a Tris buffer agent. When the complex of the present invention is used as an MRI contrast medium, the use amount varies depending upon diagnosis sites but is in the range of usually about 1μmol/kg to 10 mmmol/kg, preferably about 2 μmol/kg to about 1 mmol/kg in terms of the metal. As the method for administering the present complex, there can be cited, for example, intravenous, intra-arterial, intravesical, intramuscular and subcutaneous injections. In some cases, oral administration or direct entieral administration is also possible. Incidentally, the complex of the present invention is effective not only as a contrast medium for $T_2$ image but also as a contrast medium for $T_1$ image.

In order to obtain an MRI image, the complex of the present invention is administered to a testee in the abovementioned effective amount; imaging is conducted by a per se known method using a per se known MRI apparatus; thereby, an image of the testee can be obtained. At this time, both a $T_1$-weighted MR image and a $T_2$-weighted image can be obtained by selecting the pulse sequence. The time from the administration of the present complex to photographing differs depending upon the site for which an MRI image is taken, but is generally right after the administration to about 1 week therefrom. The optimum time can easily be determined experimentally. For example, the time for photographing of blood vessel is right after the administration to about 20 hours therefrom, preferably about 10 hours from right after the administration; the time for photographing of liver or spleen is about 15 minutes to about 1 week from after the administration, preferably about 30 minutes to about 3 days; and the time for photographing of lymph nodes is about 5 hours to about 1 week from after the administration, preferably about 10 hours to about 3 days.

EXAMPLES

The present invention is hereinafter described more specifically by way of Comparative Examples, Examples, etc.

Comparative Example 1

105 g of a carboxydextran (hereinafter abbreviated as CDX) having an intrinsic viscosity of 0.050 dl/g is dissolved in 350 ml of water. Thereto is added an aqueous solution obtained by dissolving, under nitrogen stream, 13.6 g of ferrous chloride tetrahydrate in 140 ml of a 1M aqueous ferric chloride solution (corresponding to 37.8 g of ferric chloride hexahydrate). Thereto is added 242 ml of a 3N aqueous sodium hydroxide solution in 15 minutes with heating at 80° C. and stirring. Then, the resulting solution is adjusted to pH 7.0 by adding 6N hydrochloric acid, after which the solution is heated and refluxed for 1 hour. After cooling, centrifugation is conducted at 2,100 G for 30 minutes. Ethanol is added in an amount corresponding to 78% of the supernatant volume to precipitate a complex. Centrifugation is conducted at 2,100 G for 10 minutes. The precipitate obtained is dissolved in water and dialyzed against running water for 16 hours. The dialyzate is adjusted to pH 7.2 using sodium hydroxide and concentrated under reduced pressure. The concentrate is filtered through a membrane filter (pores size: 0.2 μm) to obtain 186 ml of an intended complex aqueous sol of Comparative Example 1. Iron concentration: 52 mg/ml (iron yield: 91%), particle diameter of magnetic iron oxide: 8.4 nm, total particle diameter: 61 nm, water-soluble carboxypolysaccharide/iron weight ratio: 1.15, magnetization at 1 tesla: 98 emu/g of iron, $T_2$-relaxivity: 240 $(mM.sec)^{-1}$

Comparative Example 2

1,050 g of a CDX having an inirinsic viscosity of 0.050 dl/g is dissolved in 3,500 ml of water. Thereto is added an aqueous solution obtained by dissolving, under nitrogen stream, 136 g of ferrous chloride tetrahydrate in 1,400 ml of a 1M aqueous ferric chloride solution (corresponding to 378 g of ferric chloride hexahydrate). Thereto is added 2,420 ml of a 3N aqueous sodium hydroxide solution in 12 minutes with heating at 80° C. and stirring. Then, the resulting solution is adjusted to pH 7.1 by adding 6N hydrochloric acid, after which the solution is heated and refluxed for 2 hours. After cooling, centrifugation is conducted at 2,100 G for 30 minutes. The supernatant is filtered through a membrane filter (pore size: 1.2 μm). Water is added to make the total volume 10 l. The mixture is concentrated to 1.5 l by ultrafiltration (fractional molecular weight: 100,000 daltons). While water is being added to the concentrate, ultrafiltration (fractional molecular weight: 100,000 daltons) is conducted until the amount of the discharged liquid becomes 12 l. To the filtration inner solution is added a required amount of a CDX so that the weight ratio of CDX and iron becomes 1:1. Then, the mixture is adjusted to pH 7.0 using sodium hydroxide and subjected to centrifugation at 2,100 G for 1 hour and 30 minutes. The supernatant is filtered through a membrane filter (pore size: 0.2 μm) to obtain 1.9 l of an intended aqueous sol of Comparative Example 2. Iron concentration: 56 mg/ml (iron yield: 88%), particle diameter of magnetic iron oxide: 8.4 nm, total particle diameter: 70 nm, water-soluble carboxypolysaccharide/iron weight ratio: 1.14, magnetization at 1 tesla: 96 emu/g of iron, $T_2$-relaxivity: 232 $(mM.sec)^{-1}$

Comparative Example 3

500 ml of a solution containing 75.5 g of ferric chloride hexahydrate and 32 g of ferrous chloride tetrahydrate is added to 500 ml of a 16% ammonia water in which 250 g of a dextran having an intrinsic viscosity of 0.075 dl/g is dissolved, gradually in 5 minutes with vigorous stirring. The resulting slurry is subjected to ultrasonic grinding (30 minutes), heating (100° C., 10 minutes), cooling and centrifugation (1,0000 G, 20 minutes). The supernatant is diluted with water to make the total volume 2 l. The resulting solution is subjected to ultrafiltration (fractional molecular weight: 100,000 daltons) to concentrate to 500 ml. To the concentrate is added 1.6 l of water. The solution is subjected to ultrafiltration (fractional molecular weight: 100,000 daltons) to concentrate to 500 ml. This procedure of water addition and concentration is repeated 5 times in total. Then, to the concentrate is added 500 ml of a 1M sodium citrate solution. The mixture is dialyzed against a 10 mM ammonium citrate buffer adjusted to pH 8.2 with an ammonia water, for 16 hours. The dialyzate is concentrated to 120 ml by ultrafiltration (fractional molecular weight: 100,000 daltons). The concentrate is filtered through a membrane filter (pore size: 0.2 μm). Autoclaving is conducted at 121° C. for 30 minutes to obtain 115 ml of an intended complex aqueous sol of Comparative Example 3. Iron concentration: 57 mg/ml (iron yield: 23%), particle diameter of magnetic iron oxide: 8.1 nm, total particle diameter: 220 nm, dextran/iron weight ratio: 0.36, magnetization at 1 tesla: 83 emu/g of iron, $T_2$-relaxivity: 255 $(mM.sec)^{-1}$

Comparative Example 4

The complex obtained in Comparative Example 1 was intravenously injected to rats in an amount of 200 μmol as Fe per kg of body weight. 24 hours later, the liver, spleen and lymph nodes (of various parts of body) of each rat were taken out, and their MR images were taken and compared. In order to make easy the comparison of MR images, an ex vivo test was conducted in which the sections of the above organs and tissues were embedded in an agar phantom.

The MR image of the agar phanltom was taken at 1.5 teslas (Siemens Magnetom GBS2) by a spin-echo technique (TR 2000 ms, TE 15 ms, section thickness 2 mm). The results are shown in FIG. 1.

Figure 1:
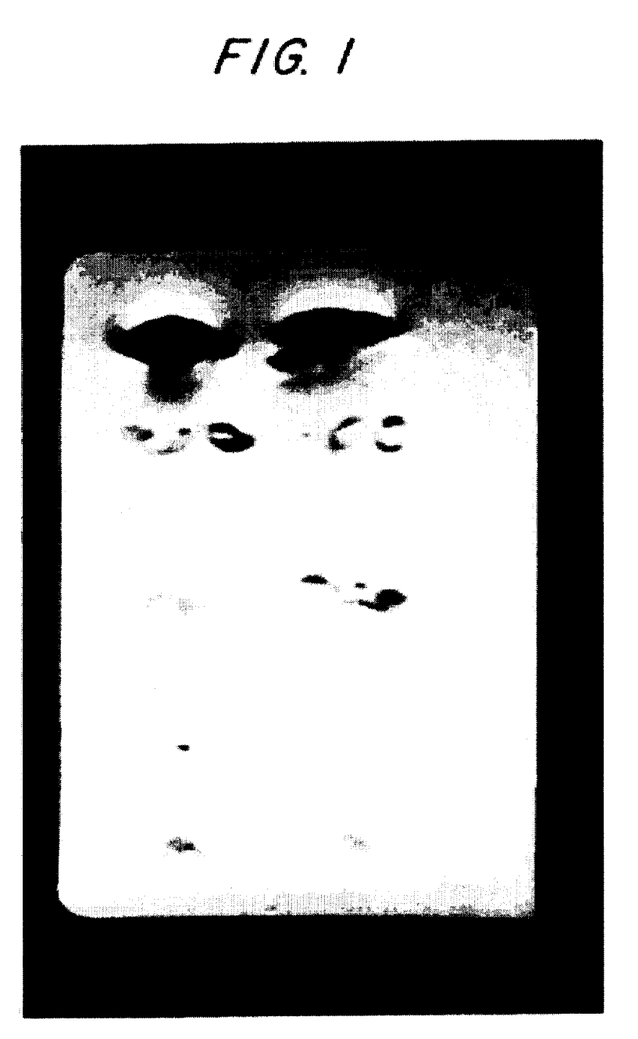
FIG. 1 is a photograph of ex vivo MR images of liver, spleen and lymph nodes of rat, taken after the complex obtained in Comparative Example 1 was injected into a rat intravenously in an amount of 200μmol (as Fe) per kg of body weight.

In FIG. 1, the arrangement of the organs and tissues embedded in the agar phantom is as follows.

| Arrangement pattern of organs and tissues in agar phantom | |
|---|---|
| Left side of photograph | Right side of photograph |
| liver | spleen |
| mandibular lymph nodes (right side of body) | mandibular lymph nodes (left side of body) |
| axillary lymph modes (right side of body) | axillary lymph modes (left side of body) |
| mesenteric lymph nodes (right side of body) | mesenteric lymph nodes (left side of body) |
| iliac lymph nodes (right side of body) | iliac lymph nodes (left side of body) |
| inguinal lymph nodes (right side of body) | inguinal lymph nodes (left side of body) |
| popliteal lymph nodes (right side of body) | popliteal lymph nodes (left side of body) |

As is clear from FIG. 1, the magnetic iron oxide complex obtained in Comparative Example 1 shows noticeable effects in liver and spleen, but shows only slight or insufficient effects in various lymph nodes.

Comparative Example 5

The blood elimination kinetics of the complex obtained in Comparative Example 1 were studied on rats.

That is, rats each having a body weight of 50 to 300 g were catheterized under ether narcosis with a 50.5 cm long polyethylene tube in the arteria carotis communis. The catheter (tube) was filled with a heparinized physiological sodium chloride solution. Each post-narcosis blood baseline value was obtained with a blood sample containing 0.41 ml of blood, 0.2 ml of the heparinized physiological sodium chloridLe solution from the tube and 0.1 ml of the heparinized physiological sodium chloride solution stored in the syringe.

After the complex obtained in Comparative Example 1 was administered in an amount of 200 μmol as Fe per kg of body weight, blood samples (blood-heparinized physiological sodium chloride solution mixtures) were taken at 5, 10, 20, 30, 60, 90, 120, 180 and 240 minutes after administration. The blood loss by the above sampling was supplemented by injection of an equal volume of a heparinized physiological sodium chloride solution.

The blood samples were diluted three-fold with distilled water; relaxation times were directly measured by the use of a pulse spectrometer (Bruk:er Minispec pc 120); and $T_1$- and $T_2$-relaxation times were determined by the inversion-recovery technique and the spin-echo technique, respectively. Kinetic parameters were calculated from baseline-corrected relaxation rates over time.

The half-lives of blood elimination after the above complex administration (200 μmol eas Fe per kg of body weight), obtained from measurement of $T_1$- and $T_2$-relaxation times were 0.78±0.28 hour and 0.72±0.34 hour, respectively, in terms of average of one-group rats (three rats).

Example 1

105 g of a CDX having an intrinsic viscosity of 0.050 dl/g is dissolved in 350 ml of water. Thereto is added an aqueous solution obtained by dissolving, under nitrogen stream, 13.6 g of ferrous chloride tetrahydrate in 140 ml of a 1M aqueous ferric chloride solution (corresponding to 37.8 g of ferric chloride hexahydrate). Thereto is added 242 ml of a 3N aqueous sodium hydroxide solution in 30 seconds with heating and stirring. Then, the resulting solution is adjusted to pH 7.0 by adding 6N hydrochloric acid, after which the solution is heated and refluxed for 1 hour. After cooling, the same procedure as in Comparative Example 1 is applied to obtain 170 ml of an intended complex aqueous sol of Example 1. Iron concentration: 59 mg/ml (iron yield: 88%), particle diameter of magnetic iron oxide: 5.8 nm, total particle diameter: 31 nm, water-soluble carboxypolysaccharide/iron weight ratio: 1.26, magnetization at 1 tesla: 77 emu/g of iron, $T_2$-relaxivity: 85 $(mM.sec)^{-1}$

Example 2

1,050 g of a CDX having an intrinsic viscosity of 0.050 dl/g is dissolved in 3,500 ml of water. Thereto is added an aqueous solution obtained by dissolving, under nitrogen stream, 136 g of ferrous chloride tetrahydrate in 1,400 ml of a 1M aqueous ferric chloride solution (corresponding to 378 g of ferric chloride hexahydrate). Thereto is added 2,420 ml of a 3N aqueous sodium hydroxide solution in 30 seconds with heating and stirring. Then, the same procedure as in Comparative Example 2 is applied to obtain 1.8 l of an intended complex aqueous sol of Example 2. Iron concentration: 57 mg/ml (iron yield: 83%), particle diameter of magnetic iron oxide: 5.7 nm, total particle diameter: 35 nm, water-soluble carboxypolysaccharide/iron weight ratio:

1.28, magnetization at 1 tesla: 75 emu/g of iron, $T_2$-relaxivity: 82 $(mM.sec)^{-1}$

Example 3

105 g of CDX having an intrinsic viscosity of 0.050 dl/g is dissolved in 350 ml of water. Thereto is added an aqueous solution obtained by dissolving, under nitrogen stream, 9.1 g of ferrous chloride tetrahydrate and 3.1 g of zinc chloride in 140 ml of a 1M aqueous ferric chloride solution (corresponding to 37.8 g of ferric chloride hexahydrate). Thereto is added 242 ml of a 3N aqueous sodium hydroxide solution in 30 seconds with heating and stirring. Then, the resulting solution is adjusted to pH 7.0 by adding 6 N hydrochloric acid, after which the solution is heated and refluxed for 1 hour. After cooling, centrifugation is conducted at 2,100 G for 30 minutes. Ethanol is added in an amount corresponding to 70% of the supernatant volume to precipitate a complex. Centrifugation is conducted at 2,100 G for 10 minutes. The precipitate obtained is dissolved in water and dialyzed against running water for 16 hours. The dialyzate is adjusted to pH 7.2 using sodium hydroxide and concentrated under reduced pressure. The concentrate is filtered through a membrane filter (pore size: 0.2 μm) to obtain 144 ml of an intended complex aqueous sol of Example 3. Iron concentration: 54 mg/ml, zinc concentration: 6 mg/ml (iron yield: 83%, zinc yield: 60%), particle diameter of magnetic iron oxide: 4.9 nm, total particle diameter: 27 nm, water-soluble carboxypolysaccharide/iron weight ratio: 1.31, magnetization at 1 tesla: 79 emu/g of metal, $T_2$-relaxivity: 84 $(mM.sec)^{-1}$

Example 4

105 g of a CDX having an intrinsic viscosity of 0.050 dl/g is dissolved in 350 ml of water. Thereto is added an aqueous solution obtained by dissolving, under nitrogen stream, 13.6 g of ferrous chloride tetrahydrate in 140 ml of a 1M aqueous ferric chloride solution (corresponding to 37.8 g of ferric chloride hexahydrate). Thereto is added 242 ml of a 3N aqueous sodium hydroxide solution in 50 seconds with heating and stirring. Then, the same procedure as in Comparative Example 1 is applied to obtain 166 ml of an intended complex aqueous sol of Example 4. Iron concentration: 57 mg/ml (iron yield: 82%), particle diameter of magnetic iron oxide: 6.8 nm, total particle diameter: 40 nm, water-soluble carboxypolysaccharide/iron weight ratio: 1.55, magnetization at 1 tesla: 79 emu/g of iron, $T_2$-relaxivity: 135 $(mM.sec)^{-1}$

Example 5

105 g of a CDX having an intrinsic viscosity of 0.050 dl/g is dissolved in 350 ml of water. Thereto is added an aqueous solution obtained by dissolving, under nitrogen stream, 13.6 g of ferrous chloride tetrahydrate in 140 ml of a 1M aqueous ferric chloride solution (corresponding to 37.8 g of ferric chloride hexahydrate). Thereto is added 242 ml of a 3N aqueous sodium hydroxide solution in 30 seconds with heating at 40° C. and stirring. Then, the same procedure as in Comparative Example 1 is applied to obtain 150 ml of an intended complex aqueous sol of Example 5. Iron concentration: 59 mg/ml (iron yield: 76%), particle diameter of magnetic iron oxide: 5.5 nm, total particle diameter: 24 nm, water-soluble carboxypolysaccharide/iron weight ratio: 1.11, magnetization at 1 tesla: 81 emu/g of iron, $T_2$-relaxivity: 82 $(mM.sec)^{-1}$

Example 6

161 g of a CDX having an intrinsic viscosity of 0.050 dl/g is dissolved in 545 ml of water. Thereto is added an aqueous solution obtained by dissolving, under nitrogen stream, 22.3 g of ferrous chloride tetrahydrate in 228 ml of a 1M aqueous ferric chloride solution (corresponding to 61.6 g of ferric chloride hexahydrate). Thereto is added 520 ml of a 28% ammonia water in 30 seconds with heating and stirring. Then, the same procedure as in Comparative Example 1 is applied to obtain 92 ml of an intended complex aqueous sol of Example 6. Iron concentration: 137 mg/ml (iron yield: 66%), particle diameter of magnetic iron oxide: 6.6 nm, total particle diameter: 43 nm, water-soluble carboxypolysaccharide/iron weight ratio: 0.72, magnetization at 1 tesla: 88 emu/g of iron, $T_2$-relaxivity: 124 $(mM.sec)^{-1}$

Example 7

105 g of a CDX having an intrinsic viscosity of 0.050 dl/g is dissolved in 350 ml of water. Thereto is added an aqueous solution obtained by dissolving, under nitrogen stream, 10.6 g of ferrous chloride tetrahydrate in 158 ml of a 1M aqueous ferric chloride solution (corresponding to 42.7 g of ferric chloride hexahydrate). Thereto is added 228 ml of a 3N aqueous sodium hydroxide solution in 30 seconds with heating and stirring. Then, the same procedure as in Comparative Example 1 is applied to obtain 202 ml of an intended complex aqueous sol of Example 7. Iron concentration: 51 mg/ml (iron yield: 91%), particle diameter of magnetic iron oxide: 5.3 nm, total particle diameter: 28 nm, water-soluble carboxypolysaccharide/iron weight ratio: 0.9, magnetization at 1 tesla: 69 emu/g of iron, $T_2$-relaxivity: 76 $(mM.sec)^{-1}$

Example 8

105 g of a CDX having an intrinsic viscosity of 0.050 dl/g is dissolved in 350 ml of water. Thereto is added an aqueous solution obtained by dissolving, under nitrogen stream, 8.3 g of ferrous chloride tetrahydrate in 168 ml of a 1M aqueous ferric chloride solution (corresponding to 45.4 g of ferric chloride hexahydrate). Thereto is added 232 ml of a 3N aqueous sodium hydroxide solution in 15 minutes with heating and stirring. Then, the same procedure as in Comparative Example 1 is applied to obtain 190 ml of an intended complex aqueous sol of Example 8. Iron concentration: 59 mg/ml (iron yield: 91%), particle diameter of magnetic iron oxide: 6.7 nm, total particle diameter: 27 nm, water-soluble carboxypolysaccharide/iron weight ratio: 0.82, magnetization at 1 tesla: 43 emu/g of iron, $T_2$-relaxivity: 52 $(mM.sec)^{-1}$

Example 9

105 g of a CDX having an intrinsic viscosity of 0.050 dl/g is dissolved in 350 ml of water. Thereto is added an aqueous solution obtained by dissolving, under nitrogen stream, 8.3 g of ferrous chloride tetrahydrate in 168 ml of a 1M aqueous ferric chloride solution (corresponding to 45.4 g of ferric chloride hexahydrate). Thereto is added 232 ml of a 3N aqueous sodium hydroxide solution in 40 seconds with heating and stirring. Then, the same procedure as in Comparative Example 1 is applied to obtain 198 ml of an intended complex aqueous sol of Example 9. Iron concentration: 54 mg/ml (iron yield: 91%), particle diameter of magnetic iron oxide: 5.3 nm, total particle diameter: 23 nm, water-soluble carboxypolysaccharide/iron weight ratio: 1.0, magnetization at 1 tesla: 73 emu/g of iron, $T_2$-relaxivity: 64 $(mM.sec)^{-1}$

Example 10

105 g of a CDX having an intrinsic viscosity of 0.050 dl/g is dissolved in 350 ml of water. Thereto is added an aqueous solution obtained by dissolving, under nitrogen stream, 4.2 g of ferrous chloride tetrahydrate in 189 ml of a 1M aqueous ferric chloride solution (corresponding to 51.0 g of ferric chloride hexahydrate). Thereto is added 240 ml of a 3N aqueous sodium hydroxide solution in 30 seconds with heating and stirring. Then, the same procedure as in Comparative Example 1 is applied to obtain 205 ml of an intended complex aqueous sol of Example 10. Iron concentration: 56 mg/ml (iron yield: 97%), particle diameter of magnetic iron oxide: 3.5 nm, total particle diameter: 21 nm, water-soluble carboxypolysaccharide/iron weight ratio: 1.4, magnetization at 1 tesla: 36 emu/g of iron, $T_2$-relaxivity: 26 $(mM.sec)^{-1}$ Example 11

162 g of a CDX having an intrinsic viscosity of 0.050 dl/g is dissolved in 1,080 ml of water. Thereto is added 353 ml of a 3N aqueous sodium hydroxide solution. There is further added an aqueous solution obtained by dissolving, under nitrogen stream, 21.6 g of ferrous chloride tetrahydrate in 222 ml of a 1M aqueous ferric chloride solution (corresponding to 44.1 g of ferric chloride hexahydrate), in 20 seconds with heating and stirring. Then, the same procedure as in Comparative Example 1 is applied to obtain 415 ml of an intended complex aqueous sol of Example 11. Iron concentration: 54 mg/ml (iron yield: 71%), particle diameter of magnetic iron oxide: 4.3 nm, total particle diameter: 46 nm, water-soluble carboxypolysaccharide/iron weight ratio: 1.1, magnetization at 1 tesla: 70 emu/g of iron, $T_2$-relaxivity: 63 $(mM.sec)^{-1}$ Example 12

For the purpose of showing the relation between the concentration of water-soluble carboxydextran-iron oxide complex and its signal intensity, the complex of the present invention obtained in Example 11 was subjected to a MRI test.

That is, 10 g of an agar (microbiology grade, Fluka, Germany) was suspended in 500 ml of double-distilled water. The suspension was heated for dissolution on a water bath, whereby a phantom was prepared. The complex of the present invention was diluted in gradually increasing concentrations to prepare test solutions, and the test solutions were placed in containers of same size. Each container was vertically fixed in the above phantom. The containers were arranged in a S-letter shape with the lowest concentration placed at upper light and the highest concentration placed at lower left. The concentrations of the test solutions were 0, 0.01, 0.05, 0.1 to 0.6 in 0.1 increments, 0.8, 1.0 and 3.0 µmol Fe/ml (total 12 concentrations).

MR images were obtained at b 1.5teslas (Siemens Magnetom GBS2) in spin-echo technique (TR 400 ms, TE 15 ms, slice thickness 1 cm). The results are shown in FIG. 2.

Figure 2:
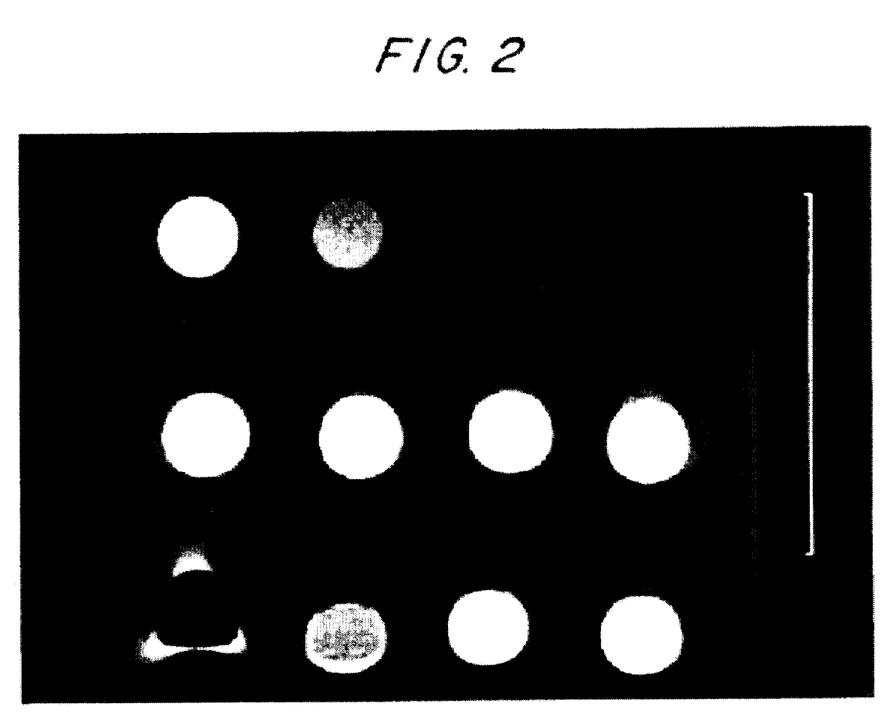
FIG. 2 is a photograph of $T_1$-weighted MR images of the complex obtained in Example 1, at various concentrations. The images are arranged in a S shape with the lowest concentration placed in the upper right and the highest concentration in the lower left.

As is clear from FIG. 2, the $T_1$-weighted image shows a marked signal-increasing effect in the concentration range of 0.2 to 0.5 µmol Fe/ml, whereas signal reduction could be observed only in the highest concentration (3.0 µmol Fe/ml). The pronounced enhancement ($T_1$-effect) seen even at low concentrations in connection with a prolonged in-blood half-life (see Example 15) indicates that the complex particles; of the present invention can favorably be used, for example, as a contrast medium for flow amount measurement of blood flow, lymph flow, etc., or for MR angiography.

Example 13

The complex obtained in Example 11 was subjected to the same test as in Comparative Example 4 to obtain MR images. The MR image of phantom obtained is shown in FIG. 3.

Figure 3:
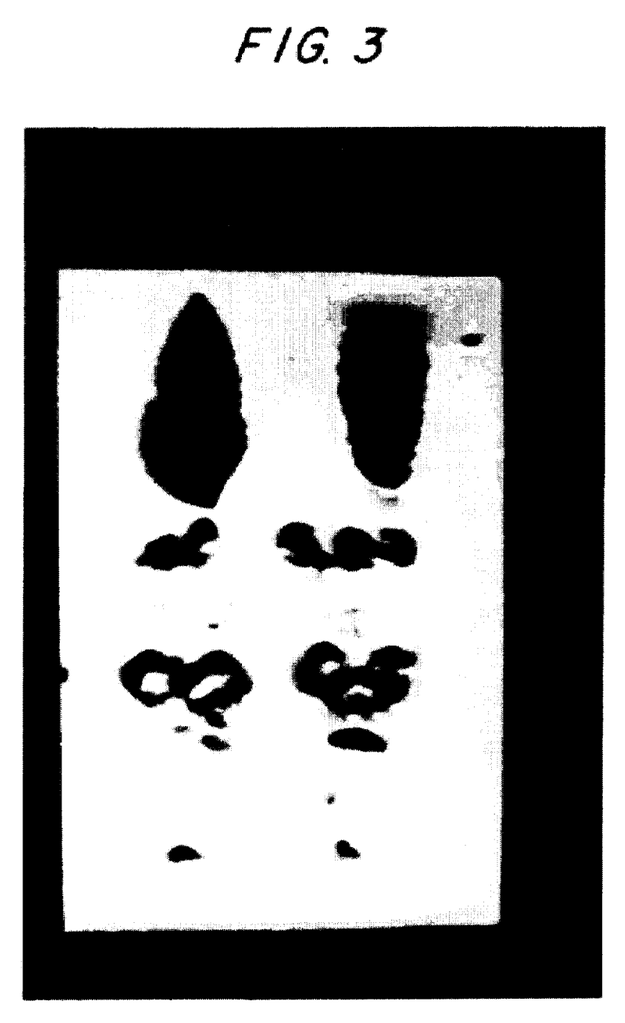
FIG. 3 is a photograph of ex vivo MR images of liver, spleen and lymph nodes of rat, taken after the complex obtained in Example 11 was injected into a rat intravenously in an amount of 200μmol (as Fe) per kg of body weight.

As is clear from FIG. 3, in the rats to which the above complex was administered in an amount of 200 µmol as Fe per kg of body weight, the signal intensities of the tested lymph nodes, particularly the mandibular, mesenteric, iliac and popliteal lymph nodes were strikingly low and a distinct imaging effect was recognized.

Example 14

The complex obtained in Example 1 was intravenously injected to rabbits in an amount of 200 µmol as Fe per kg of body weight, and in vivo MR images were taken at 1.5 teslas (Siemens Magnetom GBS.2) in gradientecho technique (TR 135 ms, TE 15 ms, slice thickness 3 mm, flip angle 15°). The results are shown in FIG. 4A and FIG. 4B.

Figure 4A:
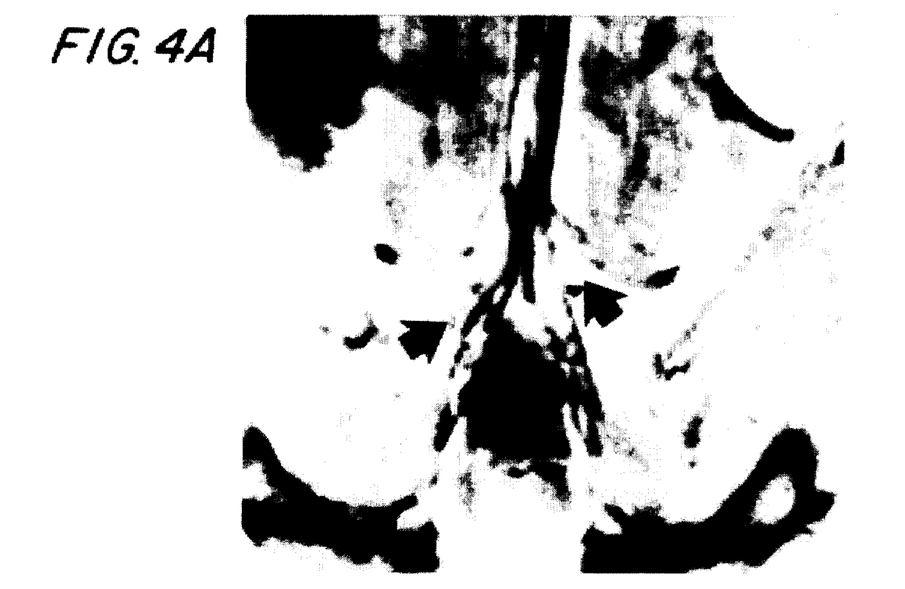
Figure 4B:
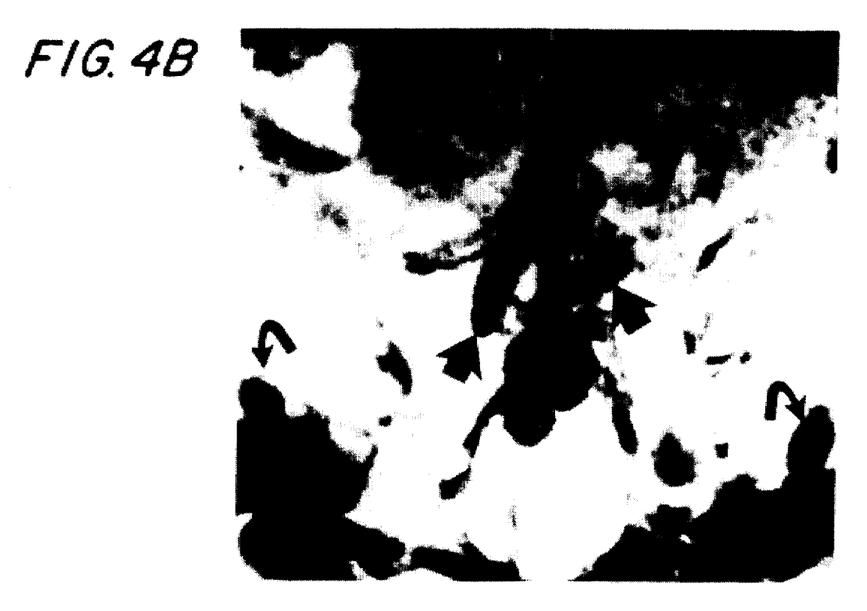

FIG. 4A is an MR image taken before the administration of the above complex, and FIG. 4B is an MR image taken 24 hours after the administration of the same complex in an amount of 200 µmol as Fe per kg of body weight. These two MR images each show the pelvic wall of rabbit.

In the image (A) before administration, lymph nodes of high signal intensity are found at the aortic bifurcation (arrows). In the image (B) after administration, uniform signal reduction is seen in the lymph nodes which showed a high signal intensity before administration (arrows) whereas supersaturation effects by the administration are seen in the bone marrow (curved arrows).

Example 15

The blood elimination kinetics of the complex obtained in Example 11 were studied by the same test method as in Comparative Example 5.

The complex obtained in Example 11 was administered to 3 rats in an amount of 200 µmol as Fe per kg of body weight, and the $T_1$- and $T_2$-relaxation times of blood samples were measured.

As a result, blood half-life, when calculated from the $T_1$-relaxation time, was 2.7±0.3 hours and, when calculated from the $T_2$-relaxation time, was 3.0±1.0 hours.

These half-lives are considerably longer than the half-lives obtained in Comparative Example 5.

We claim:

1. A water-soluble carboxypolysaccharide-magnetic iron oxide complex of small particle diameter composed of a water-soluble carboxypolysaccharide and a magnetic iron oxide having a core diameter ranging from about 2 to about 7 nm, wherein the total diameter ranges from about 10 to about 50 nm, the ratio of the total diameter to the core diameter is about 15 or less, and the $T_2$-relaxivity ranges from about 10 to about 150 $(mM.sec)^{-1}$.

2. The water-soluble carboxypolysaccharide-magnetic iron oxide complex of claim 1 composed of a water-soluble carboxypolysaccharide and a magnetic iron oxide having a core diameter ranging from about 3 to about 6 nm, wherein the total diameter ranges from about 15 to about 40 nm, the ratio of the total diameter to the core diameter is about 10 or less, and the $T_2$-relaxivity ranges from about 15 to about 120 $(mmol.sec)^{-1}$.

3. The water-soluble carboxypolysaccharide-magnetic iron oxide complex of claim 2 composed of a water-soluble carboxypolysaccharide and a magnetic iron oxide having a core diameter ranging from about 3 to about 5 nm, wherein the total diameter ranges from about 15 to about 30 nm, the ratio of the total diameter to the core diameter is about 7 or less, and the $T_2$-relaxivity ranges from about 15 to about 100 $(mmol.sec)^{-1}$.

4. The water-soluble carboxypolysaccharide-magnetic iron oxide complex of claim 1, wherein the water-soluble carboxypolysaccharide has an intrinsic viscosity ranging from 0.03 to 0.2 dl/g.

5. The water-soluble carboxypolysaccharide-magnetic iron oxide complex of claim 4, wherein the water-soluble carboxypolysaccharide is an alkali-treated polysaccharide.

6. The water-soluble carboxypolysaccharide-magnetic iron oxide complex of claim 4, wherein the water-soluble carboxypolysaccharide is selected from carboxydextran, carboxystarch and carboxypullulan.

7. The water-soluble carboxypolysaccharide-magnetic iron oxide complex of claim 5, wherein the water-soluble carboxypolysaccharide is a carboxydextran obtained by subjecting dextran to an alkali treatment.

8. An MRI contrast medium comprising the water-soluble carboxypolysaccharide-magnetic iron oxide complex of small particle diameter of claim 1.

9. An imaging or measurement method which comprises administering to a subject an effective amount of the water-soluble carboxypolysaccharide-magnetic iron oxide complex of small particle diameter of claim 1 and then conducting photographing or measurement by the use of an MR apparatus.

* * * * *